United States Patent
Lee

(10) Patent No.: US 11,596,331 B2
(45) Date of Patent: Mar. 7, 2023

(54) APPARATUS AND METHOD FOR ESTIMATING ANALYTE CONCENTRATION

(71) Applicant: SAMSUNG ELECTRONICS CO., LTD., Suwon-si (KR)

(72) Inventor: June Young Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 657 days.

(21) Appl. No.: 16/593,075

(22) Filed: Oct. 4, 2019

(65) Prior Publication Data

US 2020/0107759 A1    Apr. 9, 2020

(30) Foreign Application Priority Data

Oct. 4, 2018   (KR) .................. 10-2018-0118260

(51) Int. Cl.
  *A61B 5/1455*   (2006.01)
  *A61B 5/145*    (2006.01)
  *A61B 5/00*     (2006.01)

(52) U.S. Cl.
  CPC ........ *A61B 5/14532* (2013.01); *A61B 5/1455* (2013.01); *A61B 5/14546* (2013.01); *A61B 5/4845* (2013.01); *A61B 5/681* (2013.01); *A61B 5/7235* (2013.01); *A61B 5/7246* (2013.01); *A61B 5/7264* (2013.01); *A61B 5/7278* (2013.01); *A61B 5/0075* (2013.01)

(58) Field of Classification Search
  CPC .............. A61B 5/1455; A61B 5/14551; A61B 5/14532; A61B 5/14545; A61B 5/681; A61B 5/7271; A61B 5/7264
  See application file for complete search history.

(56) References Cited

U.S. PATENT DOCUMENTS

| | | | |
|---|---|---|---|
| 5,840,020 A | * | 11/1998 | Heinonen .......... A61B 5/14532 600/309 |
| 6,998,247 B2 | | 2/2006 | Monfre et al. |
| 7,310,542 B2 | | 12/2007 | Jeon et al. |

(Continued)

FOREIGN PATENT DOCUMENTS

| EP | 3 244 193 A1 | 11/2017 |
|---|---|---|
| EP | 3 329 848 A1 | 6/2018 |

(Continued)

OTHER PUBLICATIONS

Communication dated Sep. 28, 2021, from the European Patent Office in European Application No. 19201415.7.
Andre Perunicic, "How Are Principal Component Analysis and Singular Value Decomposition Related?", https://intoli.com/blog/pca-and-svd/, Aug. 23, 2017, pp. 1-17 (17 pages total).

(Continued)

*Primary Examiner* — Eric F Winakur
(74) *Attorney, Agent, or Firm* — Sughrue Mion, PLLC

(57) ABSTRACT

An apparatus for estimating a concentration of an analyte may include a spectrum acquisition device configured to acquire a first in vivo spectrum of an object, and a processor configured to estimate the concentration of the analyte using the first in vivo spectrum and a concentration estimation model that is generated based on a second in vivo spectrum measured during a timeframe in which the concentration of the analyte in the object is substantially constant, and update the concentration estimation model based on the first in vivo spectrum and the estimated concentration of the analyte.

20 Claims, 12 Drawing Sheets

(56) References Cited

U.S. PATENT DOCUMENTS

| | | |
|---|---|---|
| 7,460,895 B2 | 12/2008 | Arnold et al. |
| 2005/0014997 A1 | 1/2005 | Ruchti et al. |
| 2005/0159658 A1 | 7/2005 | Jeon et al. |
| 2006/0063983 A1 | 3/2006 | Yamakoshi |
| 2006/0167348 A1 | 7/2006 | Arnold et al. |
| 2008/0172205 A1 | 7/2008 | Breton et al. |
| 2012/0166092 A1 | 6/2012 | Maruo |
| 2017/0127983 A1 | 5/2017 | Spegazzini et al. |
| 2017/0319185 A1 | 11/2017 | Choi et al. |
| 2018/0146899 A1 | 5/2018 | Lee et al. |

FOREIGN PATENT DOCUMENTS

| | | |
|---|---|---|
| JP | 2010-5047 A | 1/2010 |
| JP | WO 2011/013694 A1 | 2/2011 |
| KR | 10-0634500 B1 | 10/2006 |

OTHER PUBLICATIONS

Matthew Sidley, "Calibration for real-time non-invasive blood glucose monitoring", Rochester Institute of Technology, Jun. 10, 2013, 80 pages.

Communication dated Nov. 7, 2019 issued by the European Intellectual Property Office in counterpart European Application No. 19201415.7.

Chen et al., "A unified recursive just-in-time approach with industrial near infrared spectroscopy application", Chemometrics and Intelligent Laboratory Systems, vol. 135, Apr. 22, 2014, pp. 133-140, 8 pages total, XP028850590.

Wang et al., "Effectof Path-Length Variations on PLSR Calibration Model in Noninvasive Measurement of Blood Glucose by Mid-Infrared Spectroscopy", Spectroscopy and Spectral Analysis, vol. 32, No. 4, Apr. 2012, pp. 930-933, 4 pages total.

\* cited by examiner

APPARATUS AND METHOD FOR ESTIMATING ANALYTE CONCENTRATION

CROSS-REFERENCE TO RELATED APPLICATION(S)

This application claims is based on and claims priority under 35 U.S.C. § 119 to Korean Patent Application No. 10-2018-0118260, filed on Oct. 4, 2018, in the Korean Intellectual Property Office, the disclosure of which is incorporated by reference herein in its entirety.

BACKGROUND

1. Field

The following description relates to an apparatus and method for estimating a concentration of an in vivo analyte using a bio-signal.

2. Description of Related Art

Diabetes mellitus is a chronic disease which is difficult to treat and causes various complications, and hence a blood glucose level should be checked regularly to prevent complications. When insulin is administered, blood glucose should be checked in order to prevent hypoglycemia and control the insulin dosage. Generally, measuring blood glucose requires an invasive method such as drawing blood with a finger prick. The method of measuring blood glucose in an invasive manner has high reliability of measurement, but the use of injection may cause pain during blood sampling, inconvenience, and a risk of infection. Recently, a method of non-invasive measurement of blood glucose using an optical sensor, without directly collecting blood, has been studied.

SUMMARY

Additional aspects will be set forth in part in the description which follows and, in part, will be apparent from the description, or may be learned by practice of the presented embodiments.

The following description relates to an apparatus and method for estimating a concentration of an in vivo analyte using a bio-signal.

In accordance with an aspect of the disclosure, there is provided an apparatus for estimating a concentration of an analyte may include a spectrum acquisition device configured to acquire a first in vivo spectrum of an object, and a processor configured to estimate the concentration of the analyte using the first in vivo spectrum and a concentration estimation model that is generated based on a second in vivo spectrum measured during a timeframe in which the concentration of the analyte in the object is substantially constant, and update the concentration estimation model based on the first in vivo spectrum and the estimated concentration of the analyte.

The spectrum acquisition device may acquire the first in vivo spectrum from an external device.

The spectrum acquisition device may measure the first in vivo spectrum by emitting light towards the object and receiving light reflected by or scattered from the object.

The spectrum acquisition device may measure the first in vivo spectrum using at least one of infrared spectroscopy and Raman spectroscopy.

The concentration estimation model may be generated using a net analyte signal (NAS) algorithm.

The processor may generate a spectrum for updating the concentration estimation model by correcting the first in vivo spectrum based on the estimated concentration of the analyte, extract a principal component spectrum from the generated spectrum for updating the concentration estimation model and the second in vivo spectrum used in generating the concentration estimation model, and update the concentration estimation model using the extracted principal component spectrum.

The processor may generate the spectrum for updating the concentration estimation model by removing a spectrum corresponding to a concentration change amount relative to a reference concentration of the analyte from the first in vivo spectrum.

The processor may extract the principal component spectrum from the spectrum for updating the concentration estimation model and the second in vivo spectrum used in generating the concentration estimation model by using at least one of principal component analysis (PCA), independent component analysis (ICA), non-negative matrix factorization (NMF), and singular value decomposition (SVD).

The spectrum acquisition device may acquire the second in vivo spectrum in the timeframe in which the concentration of the analyte in the object is substantially constant, and the processor may extract a principal component spectrum from the in second vivo spectrum in the timeframe in which the concentration of the analyte in the object is substantially constant, and generate the concentration estimation model based on the extracted principal component spectrum and a pure component spectrum of the analyte.

The analyte may be at least one of glucose, triglyceride, urea, uric acid, lactate, protein, cholesterol, and ethanol.

The analyte may be glucose and the timeframe in which the concentration of the analyte is substantially constant may be a fasting timeframe.

In accordance with an aspect of the disclosure, a method of estimating a concentration of an analyte may include acquiring a first in vivo spectrum of an object, estimating the concentration of the analyte based on the first in vivo spectrum and a concentration estimation model that is generated based on a second in vivo spectrum measured during a timeframe in which the concentration of the analyte in the object is substantially constant, and updating the concentration estimation model based on the first in vivo spectrum and the estimated concentration of the analyte.

The acquiring of the first in vivo spectrum may include receiving the first in vivo spectrum from an external device.

The acquiring of the first in vivo spectrum may include emitting light towards the object and measuring the first in vivo spectrum by receiving light reflected by or scattered from the object.

The measuring of the first in vivo spectrum may include measuring the first in vivo spectrum using at least one of infrared spectroscopy and Raman spectroscopy.

The concentration estimation model may be generated using a net analyte signal (NAS) algorithm.

The updating of the concentration estimation model may include generating a spectrum for updating the concentration estimation model by correcting the first in vivo spectrum based on the estimated concentration of the analyte, extracting a principal component spectrum from the generated spectrum for updating the concentration estimation model and the second in vivo spectrum used in generating the concentration estimation model, and updating the concentration estimation model using the extracted principal component spectrum.

The generating of the spectrum for updating the concentration estimation model may include generating the spectrum for updating the concentration estimation model by removing a spectrum corresponding to a concentration change amount relative to a reference concentration of the analyte from the first in vivo spectrum.

The extracting of the principal component spectrum may include extracting the principal component spectrum from the spectrum for updating the concentration estimation model and the second in vivo spectrum used in generating the concentration estimation model by using at least one of principal component analysis (PCA), independent component analysis (ICA), non-negative matrix factorization (NMF), and singular value decomposition (SVD).

The method may further include acquiring the second in vivo spectrum in the timeframe in which the concentration of the analyte in the object is substantially constant, extracting a principal component spectrum from the second in vivo spectrum in the timeframe in which the concentration of the analyte in the object is substantially constant, and generating the concentration estimation model based on the extracted principal component spectrum and a pure component spectrum of the analyte.

The analyte may be at least one of glucose, triglyceride, urea, uric acid, lactate, protein, cholesterol, and ethanol.

The analyte may be glucose, and the timeframe in which the concentration of the analyte is substantially constant may be a fasting section.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings and the detailed description, unless otherwise described, the same drawing reference numerals may refer to the same elements, features, and structures. The relative size and depiction of these elements may be exaggerated for clarity, illustration, and convenience.

DETAILED DESCRIPTION

Figure 1:
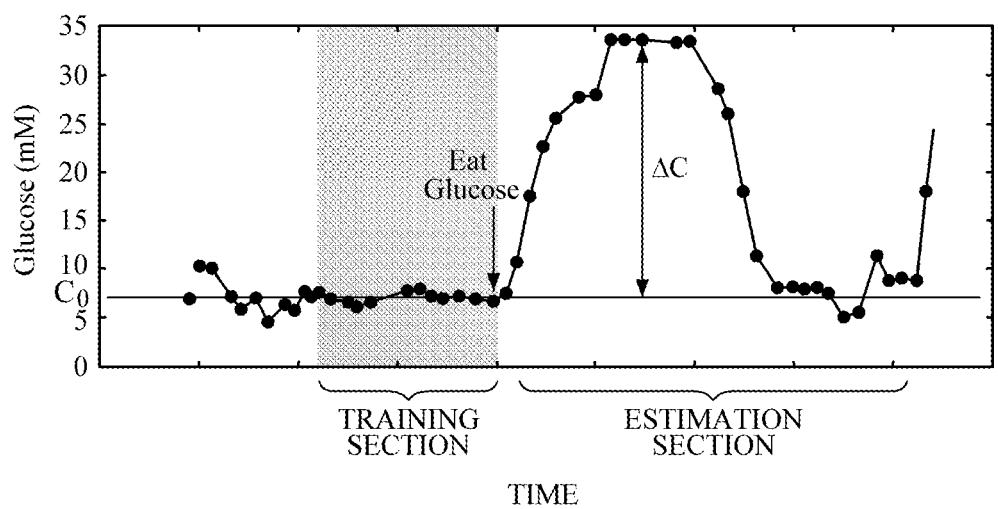
FIGS. 1 and 2 are diagrams for describing a concept of a general net analyte signal (NAS) algorithm.

The following detailed description is provided to assist the reader in gaining a comprehensive understanding of the methods, apparatuses, and/or systems described herein. Various changes, modifications, and equivalents of the systems, apparatuses, and/or methods described herein should be apparent to those of ordinary skill in the art. In the following description, a detailed description of known functions and configurations incorporated herein may be omitted so as to not obscure the subject matter of the present disclosure. Throughout the drawings and the detailed description, unless otherwise described, the same drawing reference numerals may refer to the same elements, features, and structures. The relative size and depiction of these elements may be exaggerated for clarity, illustration, and convenience.

It should be noted that in some implementations, the functions/acts noted in the blocks may occur in a different order than as shown in the flowcharts. For example, two blocks shown in succession may be executed substantially concurrently, the blocks may be executed in the reverse order, or the blocks may not be executed in succession depending upon the functionality/acts involved.

Terms described herein are selected by considering functions in the embodiment and the meanings thereof may vary depending on, for example, a user or operator's intentions or customs. Therefore, in the present disclosure, when terms are specifically defined, the meanings of terms may be interpreted based on definitions, and otherwise, may be interpreted based on general meanings recognized by those skilled in the art.

It will be understood that, although the terms "first," "second," etc. may be used herein to describe various elements, these elements might not be limited by these terms. These terms may be used to distinguish one element from another. Also, the singular forms may include the plural forms as well, unless the context clearly indicates otherwise. In the specification, unless explicitly described to the contrary, the word "comprise" and variations such as "comprises" or "comprising" should be understood to imply the inclusion of stated elements but not the exclusion of any other elements. Terms such as "unit" and "module" may denote units that process at least one function or operation, and that may be implemented in hardware, software, or a combination of hardware and software.

Figure 2:
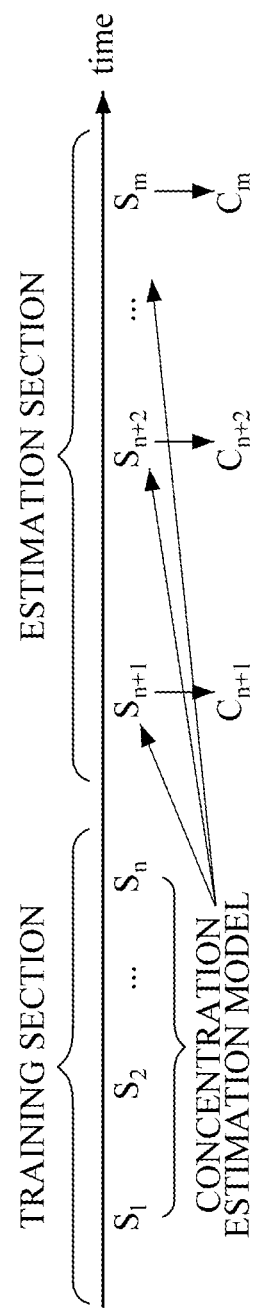

FIGS. 1 and 2 are diagrams for describing a concept of a general net analyte signal (NAS) algorithm.

Referring to FIGS. 1 and 2, a NAS algorithm may identify spectral change factors that are relatively unrelated to a concentration change of an analyte by using, as training data, in vivo spectra $S_1, S_2, \ldots,$ and $S_n$ measured during a training section, and may generate a concentration estimation model of the analyte. In addition, the NAS algorithm may estimate concentrations $C_{n+1}$, $C_{n+2}$, and $C_m$ of the analyte using in vivo spectra $S_{n+1}$, $S_{n+2}$, . . . , and $S_m$ measured during an estimation section following the training section and the concentration estimation model. In this case, the training section may be a section in which a concentration of an in vivo analyte is substantially constant. As used herein, a concentration of an in vivo analyte being "substantially constant" may refer to a change in the concentration of the in vivo analyte being less than a predetermined threshold. As an example, and referring to FIG. 1, the glucose concentration may be substantially constant in the training section because a change in the concentration is not greater than substantially five millimolar (mM). It should be understood that a threshold change value for "substantially constant" may vary depending on the underlying value that remains "substantially constant."

That is, a general NAS algorithm generates a concentration estimation model based on in vivo spectra measured during a training section, and then estimates a concentration of an analyte by applying the concentration estimation model to in vivo spectra measured during an estimation section. Thus, when at least one spectral change factor that is relatively unrelated to a concentration change of the analyte is changed by any factor, such as a temperature change of an object, a change in pressure between the object and a device, or the like, at a specific point in time during the estimation section, spectral residual may be increased from the specific point in time and thereby a blood glucose estimation error may be increased. The spectral residual may represent a difference between an in vivo spectrum reconstructed using a blood glucose estimation model and an actually measured in vivo spectrum.

Figure 3:
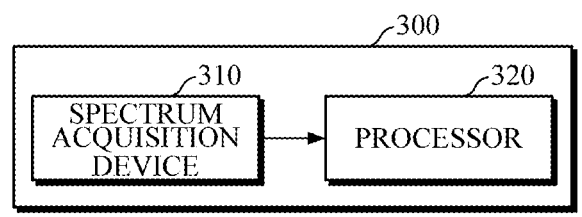
FIG. 3 is a block diagram illustrating an apparatus for estimating a concentration of an in vivo analyte according to an embodiment.

FIG. 3 is a block diagram illustrating an apparatus for estimating a concentration of an in vivo analyte according to an embodiment. The apparatus for estimating a concentration shown in FIG. 3 may be an apparatus configured to estimate a concentration of an in vivo analyte by analyzing an in vivo spectrum of an object and may be mounted in an electronic device. In this case, the electronic device may include a mobile phone, a smartphone, a tablet computer, a notebook computer, a personal digital assistant (PDA), a portable multimedia player (PMP), a navigation system, an MP3 player, a digital camera, a wearable device, and the like. The wearable device may include a wrist watch type, a wrist band type, a ring type, a belt type, a necklace type, an ankle band type, a thigh band type, a forearm band type, and the like. However, the electronic device and the wearable device are not limited to the above-described examples.

Referring to FIG. 3, the apparatus 300 for estimating a concentration of an in vivo analyte may include a spectrum acquisition device 310 and a processor 320.

The spectrum acquisition device 310 may acquire an in vivo spectrum of an object. For example, the spectrum acquisition device 310 may acquire an in vivo spectrum (hereinafter referred to as an "in vivo spectrum for training") measured during a section (e.g., timeframe) in which a concentration of an analyte in the object is substantially constant and/or an in vivo spectrum (hereinafter referred to as an "in vivo spectrum for estimation") measured during a section (e.g., timeframe) to estimate a concentration of the analyte in the object.

According to an embodiment, the spectrum acquisition device 310 may acquire an in vivo spectrum by receiving the in vivo spectrum from an external device that measures and/or stores the in vivo spectrum. In this case, the spectrum acquisition device 310 may use various communication technologies, such as Bluetooth communication, Bluetooth low energy (BLE) communication, near field communication (NFC), wireless local access network (WLAN) communication, ZigBee communication, infrared data association (IrDA) communication, wireless-fidelity (Wi-Fi) communication, ultra-wideband (UWB) communication, Ant+ communication, Wi-Fi direct (WFD) communication, radio frequency identification (RFID) communication, third generation (3G) communication, fourth generation (4G) communication, and fifth generation (5G) communication.

According to an embodiment, the spectrum acquisition device 310 may emit light towards the object and directly measure an in vivo spectrum by receiving light reflected by or scattered from the object, thereby acquiring the in vivo spectrum. In this case, the spectrum acquisition device 310 may use infrared spectroscopy, Raman spectroscopy, or the like, and may measure the in vivo spectrum using various spectroscopy methods. To this end, the spectrum acquisition device 310 may include a light source configured to emit light towards the object, and a photodetector configured to receive light reflected by or scattered from the object and detect a bio-spectrum. Here, the light source may emit a near-infrared ray (NIR) or a mid-infrared ray (MIR) towards the object. However, a wavelength of light to be emitted from the light source may vary according to the purpose of measurement or the type of the analyte. In addition, the light source may not be necessarily formed as a single light emitter, and instead may be formed as a group of light emitters. The light source may be formed as a light emitting diode (LED), a laser diode, a phosphor, and the like. The photodetector may be formed by a photodiode, a phototransistor, a charge-coupled device (CCD), and the like. The photodetector may be formed as a single device, or may be configured in the form of an array including a plurality of devices. The numbers and arrangement of light sources and photodetectors may vary and may be changed according to the type of the analyte, the purpose of application, and a size and a shape of the electronic device in which the apparatus 300 for estimating a concentration of an in vivo analyte is mounted.

The processor 320 may generate and update a concentration estimation model, may process various signals, and may perform operations associated with estimation of an analyte concentration.

The processor 320 may acquire the in vivo spectrum for training and/or the in vivo spectrum for estimation by controlling the spectrum acquisition device 310 at predetermined intervals or in response to a user request.

When a plurality of in vivo spectra for training are acquired during a section in which a concentration of the analyte in the object is not substantially changed, the processor 320 may generate a concentration estimation model based on the plurality of acquired in vivo spectra for training. In this case, the analyte may include glucose, triglyceride, urea, uric acid, lactate, protein, cholesterol, ethanol, and the like. In the case where the in vivo analyte is glucose, a concentration of the analyte may correspond to a blood glucose level and a section in which the concentration of the analyte is substantially constant may correspond to a fasting section in which glucose is not substantially introduced into the blood. Hereinafter, for convenience of description, the following description will be made based on an embodiment where the analyte is glucose.

According to an embodiment, the processor 320 may generate a concentration estimation model using a NAS algorithm and a plurality of in vivo spectra for training that are measured during a fasting section. More specifically, the processor 320 may identify spectral change factors that are relatively unrelated to a concentration change of the analyte by using, as training data, the plurality of in vivo spectra for training that are measured during a fasting section. For example, the processor 320 may extract a principal component spectrum from the plurality of in vivo spectra for training that are measured during the fasting section using various dimensional reduction algorithms, such as principal component analysis (PCA), independent component analysis (ICA), non-negative matrix factorization (NMF), singular value decomposition (SVD), and the like. In addition, the processor 320 may generate the concentration estimation model based on the result of training, that is, the extracted principal component spectrum. In this case, the generated concentration estimation model may be represented by Equation 1 and Equation 2 shown below.

$$S_m = \sum_i a_i \times S_{pc,i} + \varepsilon_g \times L \times \Delta C \quad \text{Equation (1)}$$

$$C_m = \Delta C + C_0 \quad \text{Equation (2)}$$

Here, $C_m$ may denote a concentration of an analyte, $C_0$ may denote a reference concentration of the analtye (e.g., a concentration of the analyte during a fasting section), $\Delta C$ may denote an amount of change in concentration relative to $C_0$, $S_m$ may denote an in vivo spectrum for estimation, $S_{pc,i}$ may denote a principal component spectrum, a may denote a degree to which each principal component spectrum contributes to the in vivo spectrum for estimation, $\varepsilon_g$ may denote a spectrum (hereinafter referred to as a "pure component spectrum") of the analyte of a unit concentration (e.g., 1 mM), and L may denote an optical pathlength. Here, may be experimentally obtained.

When the in vivo spectrum for estimating a concentration of the analyte is obtained after the concentration estimation model is generated, the processor 320 may estimate a concentration of the analyte using the in vivo spectrum and the concentration estimation model. For example, the processor 320 may calculate $\Delta C$ by applying a regression analysis algorithm (e.g., a least square method) to Equation 1, and estimate a concentration of the analyte using Equation 2. In the process of calculating $\Delta C$ by applying the regression analysis algorithm, a, may also be calculated.

When the estimation of a concentration of the analyte is completed by analyzing the in vivo spectrum for estimation, the processor 320 may update the concentration estimation model based on the in vivo spectrum for estimation used in concentration estimation and the estimated concentration.

According to an embodiment, the processor 320 may generate a spectrum for updating the concentration estimation model by correcting the in vivo spectrum for estimation based on the estimated concentration. For example, the processor 320 may generate the spectrum for updating the concentration estimation model by removing a spectrum corresponding to the amount of change in concentration relative to the reference concentration of the analyte from the in vivo spectrum for estimation. This process may be represented as Equation 3 shown below.

$$S_u = S_m - \varepsilon_g \times L \times \Delta C = S_m - \varepsilon_g \times L \times (C_m - C_0) \quad \text{Equation (3)}$$

Here, $S_u$ may denote a spectrum for updating the concentration estimation model, $S_m$ may denote an in vivo spectrum for estimation, $\varepsilon_g$ may denote a pure component spectrum of the analyte, L may denote an optical pathlength, $C_m$ may denote an estimated concentration of the analyte, $C_0$ may denote a reference concentration of the analyte (e.g., a concentration of the analyte during a fasting section), and $\Delta C$ may denote an amount of change in concentration relative to $C_0$.

In addition, the processor 320 may identify a spectral change factor that is relatively unrelated to the concentration change of the analyte by using, as training data, the generated spectrum for updating the concentration estimation model and the plurality of in vivo spectra for training used in generating the concentration estimation model. For example, the processor 320 may re-extract a principal component spectrum from the spectrum for updating the concentration estimation model, and the plurality of in vivo spectra for training used in generating the concentration estimation model by using various dimensional reduction algorithms, such as PCA, ICA, NMF, and SVD. In addition, the processor 320 may update the concentration estimation model using the result of training, that is, the re-extracted principal component spectrum. That is, in Equation 1, the principal component spectrum $S_{pc,i}$ may be replaced with the principal component spectrum that is re-extracted.

As described above, the apparatus 300 for estimating a concentration according to an embodiment may estimate a concentration of the analyte and update a blood glucose estimation model based on the estimated concentration and an in vivo spectrum at the time of estimation to improve the accuracy of blood glucose prediction by reflecting, in real time, the influences of spectral change factors that are relatively unrelated to the concentration change of the analyte.

Figure 4:
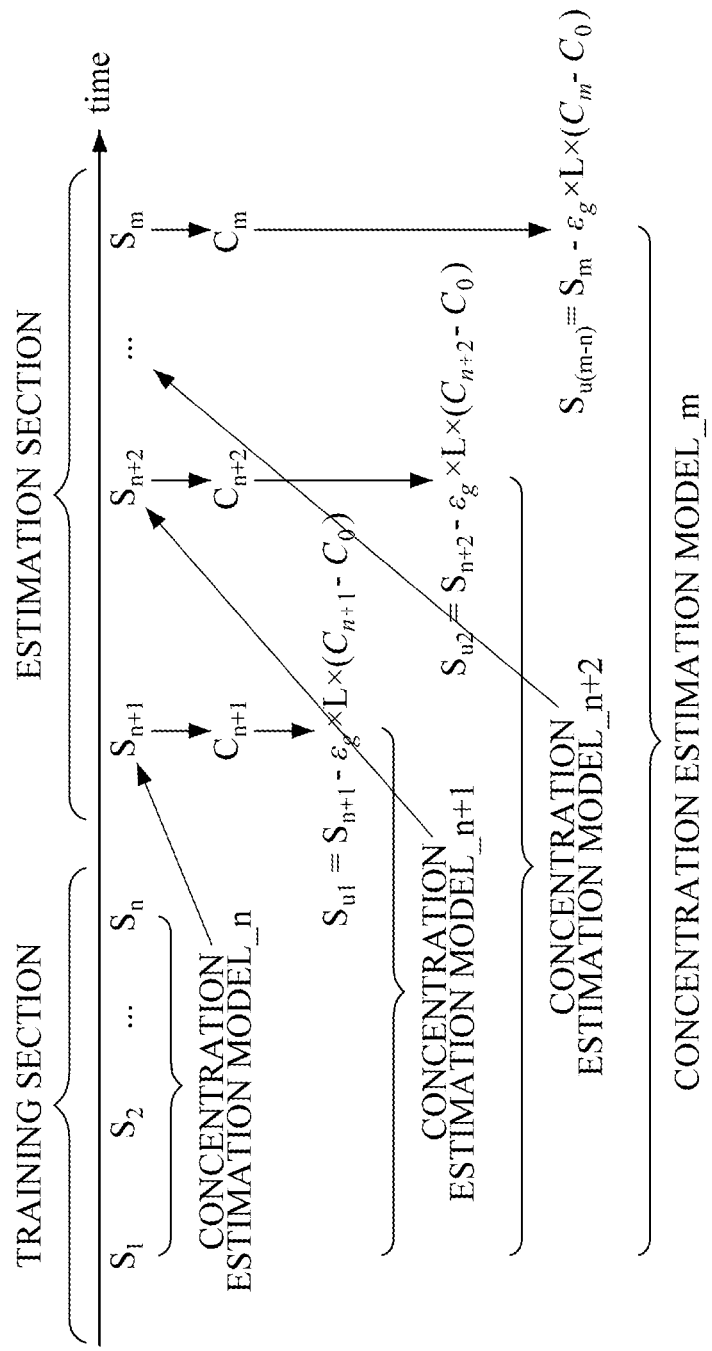
FIG. 4 is a diagram for describing a method of updating a concentration estimation model according to an embodiment.

FIG. 4 is a diagram for describing a method of updating a concentration estimation model according to an embodiment.

Referring to FIGS. 3 and 4, the processor 320 may identify spectral change factors that are relatively unrelated to a concentration change of an analyte by using, as training data, in vivo spectra $S_1, S_2, \ldots,$ and $S_n$ measured during a training section (e.g., a fasting section) and generate a concentration estimation model_n based on the result of training.

When an in vivo spectrum $S_{n+1}$ is measured, the processor 320 may estimate a concentration $C_{n+1}$ of the analyte using the in vivo spectrum $S_{n+1}$ and the concentration estimation model_n, and generate a spectrum $S_{u1}$ for updating the concentration estimation model_n by correcting the in vivo spectrum $S_{n+1}$ based on the estimated concentration $C_{n+1}$.

The processor 320 may identify the spectral change factors that are relatively unrelated to the concentration change of the analyte by using, as training data, the in vivo spectra $S_1, S_2, \ldots,$ and $S_n$ used in generating the concentration estimation model_n and the spectrum $S_{u1}$ for updating the concentration estimation model_n, and generate a concentration estimation model_n+1 by updating the concentration estimation model_n based on a result of training.

When an in vivo spectrum $S_{n+2}$ is measured, the processor 320 may estimate a concentration $C_{n+2}$ of the analyte using the in vivo spectrum $S_{n+2}$ and the concentration estimation model_n+1, and generate a spectrum $S_{u2}$ for updating the concentration estimation model_n+1 by correcting the in vivo spectrum $S_{n+2}$ based on the estimated concentration $C_{n+2}$.

The processor 320 may identify the spectral change factors that are relatively unrelated to the concentration change of the analyte by using, as training data, the in vivo spectra $S_1, S_2, \ldots, S_n$ used in generating the concentration estimation model_n+1, the spectrum $S_{u1}$ for updating the concentration estimation model_n+1, and the spectrum $S_{u2}$ for updating the concentration estimation model_n+1, and generate a concentration estimation model_n+2 by updating the concentration estimation model_n+1 based on the result of training.

In this manner, the processor 320 may repeatedly and iteratively update the concentration estimation model in real time based on the measured in vivo spectrum and the estimated concentration.

Figure 5:
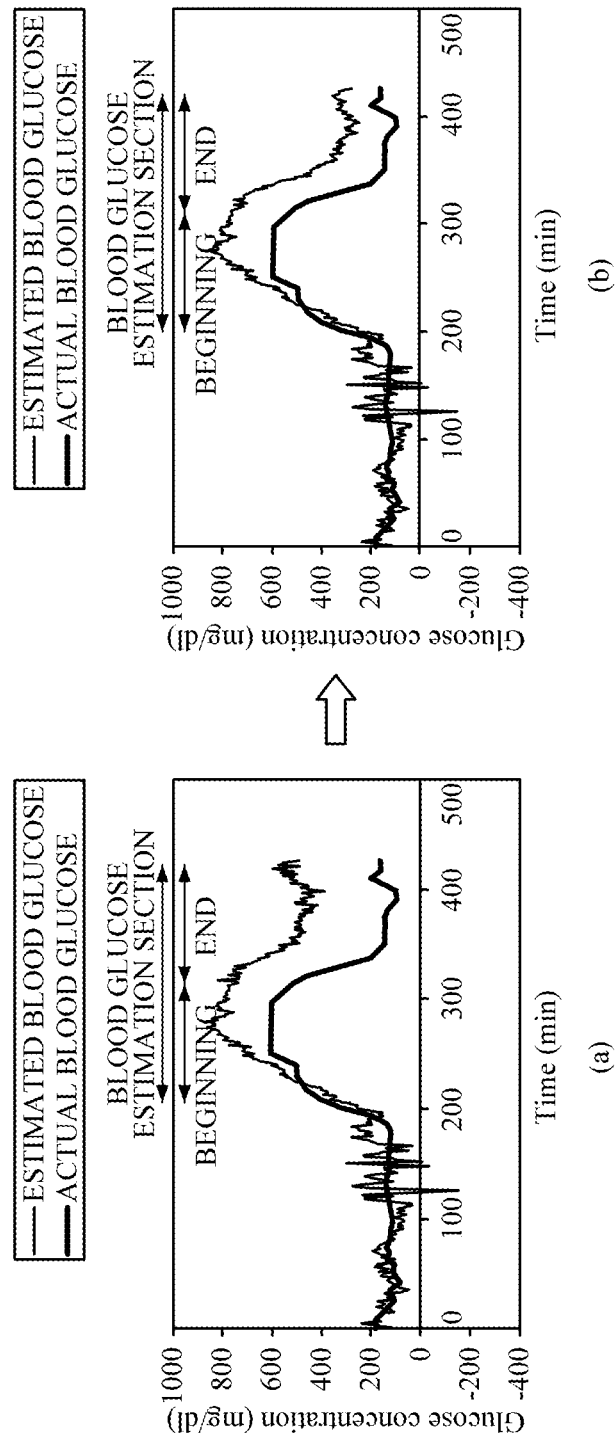
FIG. 5 illustrates graphs showing a comparison of a blood glucose value estimated using a general NAS algorithm and a blood glucose value estimated using a concentration estimation method in accordance with an embodiment.

FIG. 5 illustrates graphs showing a comparison of a blood glucose value estimated using a general NAS algorithm and a blood glucose value estimated using a concentration estimation method in accordance with an embodiment. The left graph (a) in FIG. 5 shows a blood glucose value estimated using a general NAS algorithm, and the right graph (b) shows a blood glucose value estimated using a blood glucose estimation method according to an embodiment.

Referring to FIG. 5, it is seen that at the beginning of a blood glucose estimation section, an error between a blood glucose value estimated using the general NAS algorithm and an actual blood glucose value is almost the same as an error between a blood glucose value estimated using a blood glucose estimation method according to an embodiment and an actual blood glucose value. However, it is seen that at the end of the blood glucose estimation section, the error between the blood glucose value estimated using the blood estimation method according to an embodiment and the actual blood glucose value is less than an error between the actual blood glucose value and the blood glucose value estimated using the general NAS algorithm.

Figure 6:
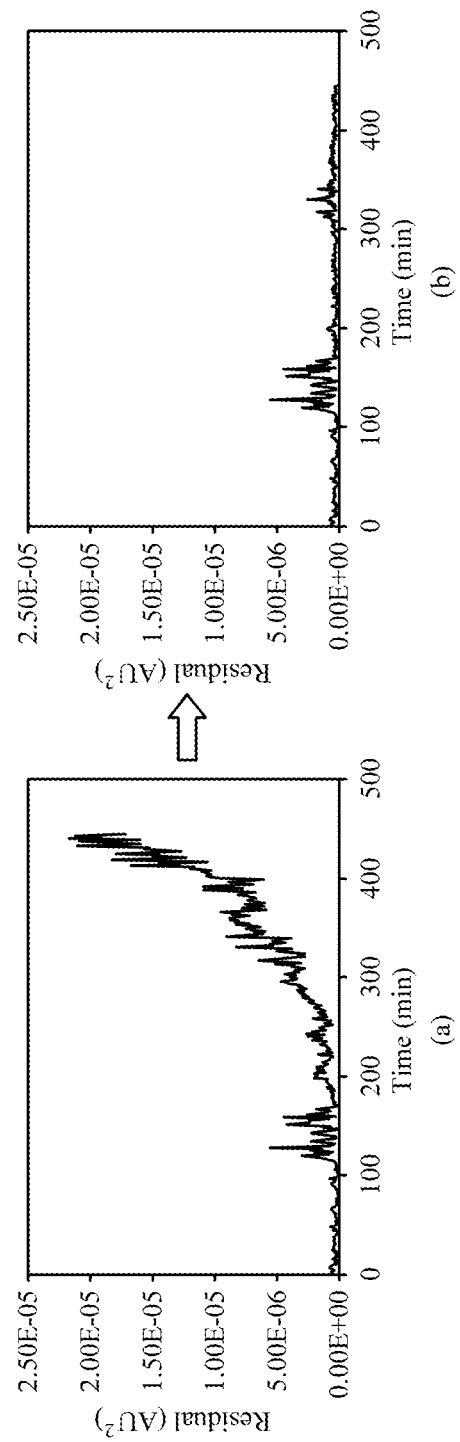
FIG. 6 illustrates graphs showing a comparison of spectral residual in the case of a general NAS algorithm and spectral residual in the case of a blood glucose estimation method according to an embodiment.

FIG. 6 illustrates graphs showing a comparison of spectral residual in the case of a general NAS algorithm, and spectral residual in the case of a blood glucose estimation method according to an embodiment. In FIG. 6, the left graph (a) shows the spectral residual in the case of a general NAS algorithm and the right graph (b) shows the spectral residual in the case of the blood glucose estimation method according to an embodiment.

Referring to FIG. 6, it can be seen that the spectral residual in the case of the general NAS algorithm increases over time. On the other hand, it is seen that the spectral residual is maintained at a substantially constant value when the blood glucose estimation method according to an embodiment is used. That is, it can be seen that the increase in spectral residual with time can be suppressed by using the blood glucose estimation method according to an embodiment, and thereby the accuracy of blood glucose estimation can be improved.

Figure 7:
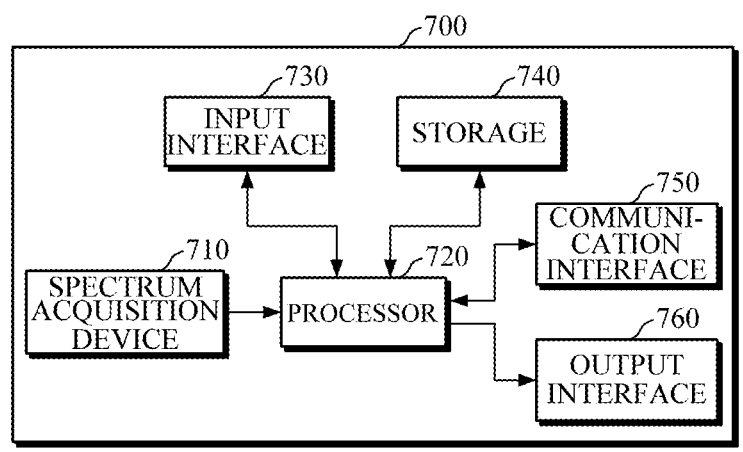
FIG. 7 is a block diagram illustrating an apparatus for estimating a concentration of an in vivo analyte according to an embodiment.

FIG. 7 is a block diagram illustrating an apparatus for estimating a concentration of an in vivo analyte according to an embodiment. The apparatus of FIG. 7 to estimate a concentration of an in vivo analyte may be an apparatus configured to estimate a concentration of an analyte by analyzing an in vivo spectrum of an object, and may be mounted in the above-described various electronic devices.

Referring to FIG. 7, the apparatus 700 for estimating a concentration may include a spectrum acquisition device 710, a processor 720, an input interface 730, a storage 740, a communication interface 750, and an output interface 760. Here, the spectrum acquisition device 710 and the processor 720 may be respectively the same as the spectrum acquisition device 310 and the processor 320 as described above with reference to FIG. 3, and thus detailed descriptions thereof may be omitted.

The input interface 730 may receive various operation signals based on a user input. According to an embodiment, the input interface 730 may include a key pad, a dome switch, a touch pad (e.g., a resistive touch pad, a capacitive touch pad, and the like), a jog wheel, a jog switch, a hardware button, and the like. In particular, when a touch pad has a layered structure with a display, the structure may be referred to as a touch screen.

A program or commands for operations of the apparatus 700 for estimating a concentration of an in vivo analyte may be stored in the storage 740, and data input to and output from the apparatus 700 may be stored in the storage 740. In addition, an in vivo spectrum, a concentration estimation model, and an estimated concentration value of an analyte may be stored in the storage 740. The storage 740 may include at least one type of storage medium, such as a flash memory type, a hard disk type, a multimedia card micro type, a card type memory (e.g., a secure digital (SD) or eXtreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, and the like. In addition, the apparatus 700 for estimating a concentration may communicate with an external storage medium, such as a web storage that performs the storage function of the storage 740 via the Internet.

The communication interface 750 may communicate with an external device. For example, the communication interface 750 may transmit data input to, data stored in, and data processed by the apparatus 700 for estimating a concentration to the external device, or may receive a variety of data to generate and update a concentration estimation model and to estimate a concentration of the analyte from the external device.

In this case, the external device may be a medical device that uses the data input to, data stored in, and/or data processed by the apparatus 700 for estimating a concentration, or may be a printer or a display device to output a result. In addition, the external device may be a digital television (TV), a desktop computer, a mobile phone, a smartphone, a tablet computer, a notebook computer, a PDA, a PMP, a navigation system, an MP3 player, a digital camera, a wearable device, or the like, but is not limited thereto.

The communication interface 750 may communicate with the external device using a communication technology, such as Bluetooth communication, BLE communication, NFC, WLAN communication, ZigBee communication, IrDA communication, WFD communication, UWB communication, Ant+ communication, Wi-Fi communication, RFID communication, 3G communication, 4G communication, and 5G communication. However, these are examples, and the communication technology is not limited thereto.

The output interface 760 may output data input to, data stored in, and data processed by the apparatus 700 for estimating a concentration of an in vivo analyte. According to an embodiment, the output interface 760 may output the data input to, the data stored in, and the data processed by the apparatus 700 using at least one of an audible method, a visual method, and a tactile method. To this end, the output interface 760 may include a speaker, a display, a vibrator, and the like.

Figure 8:
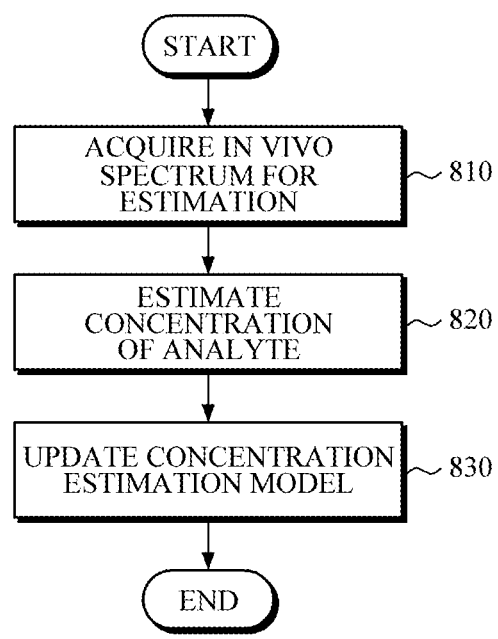
FIG. 8 is a flowchart illustrating a method of estimating a concentration of an in vivo analyte according to an embodiment.

FIG. 8 is a flowchart illustrating a method of estimating a concentration of an in vivo analyte according to an embodiment. The method of FIG. 8 may correspond to a method performed by the apparatuses 300 and 700 of FIGS. 3 and 7, respectively, to estimate a concentration.

Referring to FIG. 8, the apparatus for estimating a concentration of an in vivo analyte may acquire an in vivo spectrum for estimation for an object (operation 810). According to an embodiment, the apparatus for estimating a concentration may receive the in vivo spectrum from an external device which measures and/or stores the in vivo spectrum, or may emit light towards the object and directly measure an in vivo spectrum by receiving light reflected by or scattered from the object, thereby acquiring the in vivo spectrum. For example, the apparatus for estimating a concentration of an in vivo analyte may receive the in vivo spectrum from the external device using various communication technologies, or may directly measure the in vivo spectrum using infrared spectroscopy, Raman spectroscopy, or the like.

The apparatus for estimating a concentration may estimate a concentration of the analyte using the acquired in vivo spectrum for estimation and the concentration estimation model (operation 820). For example, the apparatus for estimating a concentration may estimate the concentration of the analyte using Equation 1 and Equation 2 as described elsewhere herein.

When estimation of the concentration of the analyte is completed, the apparatus for estimating a concentration may update the concentration estimation model based on the in vivo spectrum for estimation used in estimating the concentration and the estimated concentration (operation 830).

Figure 9:
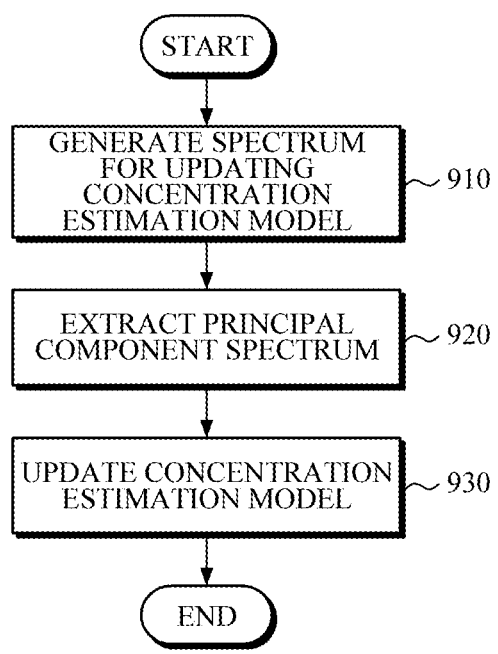
FIG. 9 is a flowchart illustrating a method of updating a concentration estimation model according to an embodiment.

FIG. 9 is a flowchart illustrating a method of updating a concentration estimation model according to an embodiment. The method of FIG. 9 may correspond to an embodiment of operation 830 of FIG. 8 to update the concentration estimation model.

Referring to FIG. 9, an apparatus for estimating a concentration of an in vivo analyte may generate a spectrum for updating a concentration estimation model by correcting an in vivo spectrum for estimation based on an estimated concentration of the analyte (operation 910). According to an embodiment, the apparatus for estimating a concentration may generate the spectrum for updating the concentration estimation model by removing a spectrum corresponding to a change in concentration amount relative to a reference concentration of an analyte from the in vivo spectrum for estimation. For example, the apparatus for estimating a concentration may generate the spectrum for updating the concentration estimation model using Equation 3 described elsewhere herein.

The apparatus for estimating a concentration may extract a principal component spectrum from the generated spectrum for updating the concentration estimation model and a plurality of in vivo spectra for training used in generating the concentration estimation model (operation 920). For example, the apparatus for estimating a concentration may extract a principal component spectrum from the spectrum for updating the concentration estimation model and the plurality of in vivo spectra for training used in generating the concentration estimation model by using various dimensional reduction algorithms, such as PCA, ICA, NMF, and SVD.

The apparatus for estimating a concentration may update the concentration estimation model using the extracted principal component spectrum (operation 930). Specifically, and referring to Equation 1 shown elsewhere herein, the principal component spectrum $S_{pc,i}$ may be replaced with the principal component spectrum extracted in operation 920.

Figure 10:
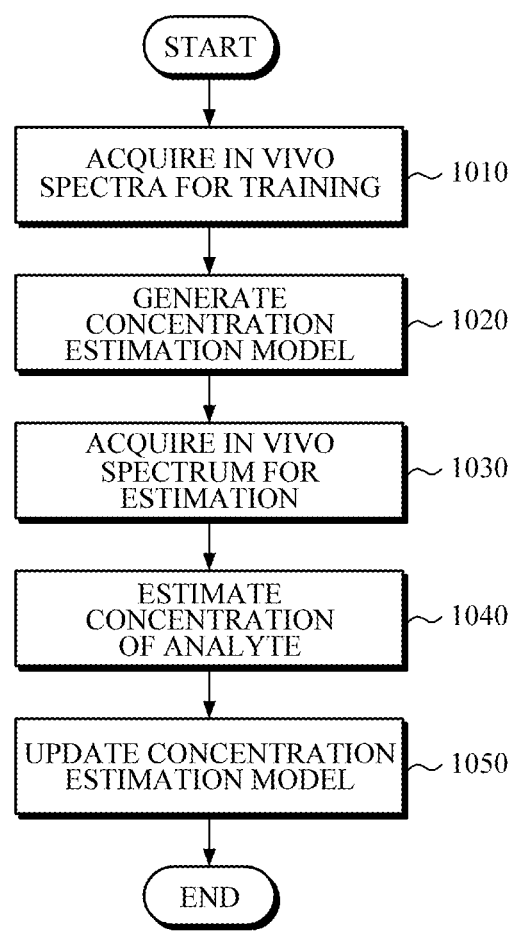
FIG. 10 is a flowchart illustrating a method of estimating a concentration of an in vivo analyte according to an embodiment.

FIG. 10 is a flowchart illustrating a method of estimating a concentration of an in vivo analyte according to an embodiment. The method of FIG. 10 may correspond to a method performed by the apparatuses 300 and 700 of FIGS. 3 and 7, respectively, to estimate a concentration.

Referring to FIG. 10, an apparatus for estimating a concentration of an in vivo analyte may acquire a plurality of in vivo spectra for training that are measured during a section in which a concentration of an analyte in an object is not substantially changed (operation 1010). According to an embodiment, the apparatus for estimating a concentration may receive in vivo spectra from an external device that measures and/or stores the in vivo spectra, or may emit light towards the object and directly measure the in vivo spectra by receiving light reflected by or scattered from the object, thereby acquiring the in vivo spectra for training.

When the plurality of in vivo spectra for training are acquired, the apparatus for estimating a concentration may generate a concentration estimation model based on the plurality of acquired in vivo spectra for training (operation 1020). According to an embodiment, the apparatus for estimating a concentration may generate the concentration estimation model using a NAS algorithm and the plurality of in vivo spectra for training. For example, the apparatus for estimating a concentration may extract a principal component spectrum from the plurality of in vivo spectra for training using the above-described various dimensional reduction algorithms. In addition, the apparatus for estimating a concentration of an in vivo analyte may generate the concentration estimation model based on the extracted principal component spectrum. In this case, the generated concentration estimation model may be represented by Equation 1 and Equation 2 as described elsewhere herein.

The apparatus for estimating a concentration may acquire an in vivo spectrum for estimation for the object after generating the concentration estimation model (operation 1030). According to an embodiment, the apparatus for estimating a concentration may receive the in vivo spectrum from an external device that measures and/or stores the in vivo spectrum, or may emit light towards the object and directly measure the in vivo spectrum by receiving light reflected by or scattered from the object, thereby acquiring the in vivo spectrum for estimation.

The apparatus for estimating a concentration may estimate a concentration of the analyte using the acquired in vivo spectrum for estimation and the concentration estimation model (operation 1040). For example, the apparatus for estimating a concentration may estimate the concentration of the analyte using Equation 1 and Equation 2 as described elsewhere herein.

When estimation of the concentration of the analyte is completed, the apparatus for estimating a concentration may update the concentration estimation model based on the in vivo spectrum for estimation used in estimating the concentration and the estimated concentration (operation 1050).

Figure 11:
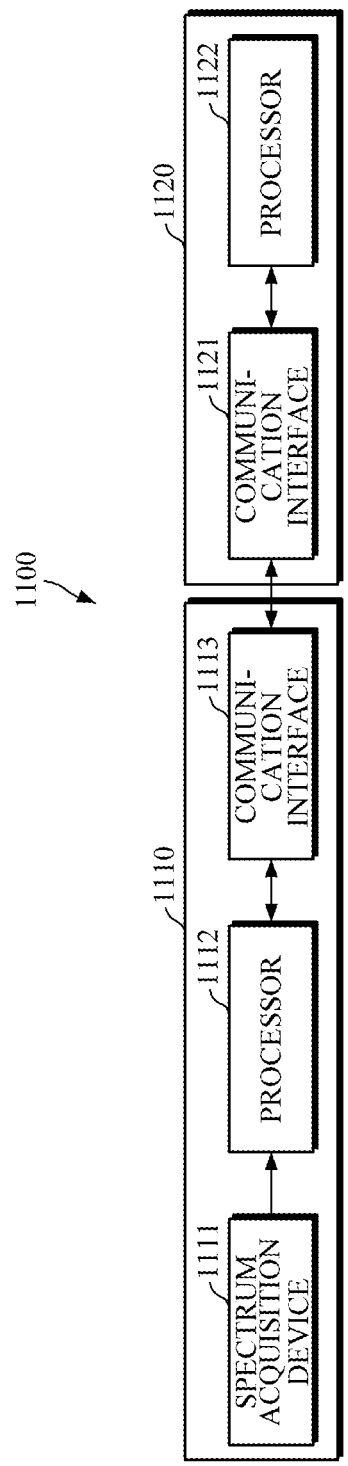
FIG. 11 is a block diagram illustrating a system for estimating a concentration of an in vivo analyte according to an embodiment.

FIG. 11 is a block diagram illustrating a system for estimating a concentration of an in vivo analyte according to an embodiment. The system 1100 of FIG. 11 to estimate a concentration may be an embodiment in which the concentration estimation function and the concentration estimation model generation/update functions, which are described with reference to FIGS. 3 through 10, are performed in separate apparatuses. The concentration estimation function may be performed by an apparatus 1110 for estimating a concentration, and the concentration estimation model generation/update functions may be performed by an apparatus 1120 for generating a model.

More specifically, the apparatus 1110 for estimating a concentration may measure an in vivo spectrum for training by emitting light towards an object via a spectrum acquisition device 1111 during a section in which a concentration of an analyte in the object is not substantially changed, and receiving light reflected by or scattered from the object, and may transmit the measured in vivo spectrum for training to the apparatus 1120 for generating a model via a communication interface 1113.

The apparatus 1120 for generating a model may receive the in vivo spectrum for training from the apparatus 1110 for estimating a concentration via a communication interface 1121, and generate a concentration estimation model using the in vivo spectrum for training via a processor 1122. In addition, the apparatus 1120 for generating a model may transmit the generated concentration estimation model to the apparatus 1110 for estimating a concentration via the communication interface 1121.

The apparatus 1110 for estimating a concentration may receive the concentration estimation model from the apparatus 1120 for generating a model via the communication interface 1113 and measure an in vivo spectrum for estimation by emitting light towards the object via the spectrum acquisition device 1111 and receiving light reflected by or scattered from the object. In addition, the apparatus 1110 for estimating a concentration may estimate a concentration of the analyte using the in vivo spectrum for estimation and the concentration estimation model via a processor 1112 and transmit the estimated concentration and the in vivo spectrum for estimation to the apparatus 1120 for generating a model.

The apparatus 1120 for generating a model may receive the estimated concentration and the in vivo spectrum for estimation via the communication interface 1121, and may update the concentration estimation model via the processor 1122. In addition, the apparatus 1120 for generating a model may transmit the updated concentration estimation model to the apparatus 1110 for estimating a concentration via the communication interface 1121.

Figure 12:
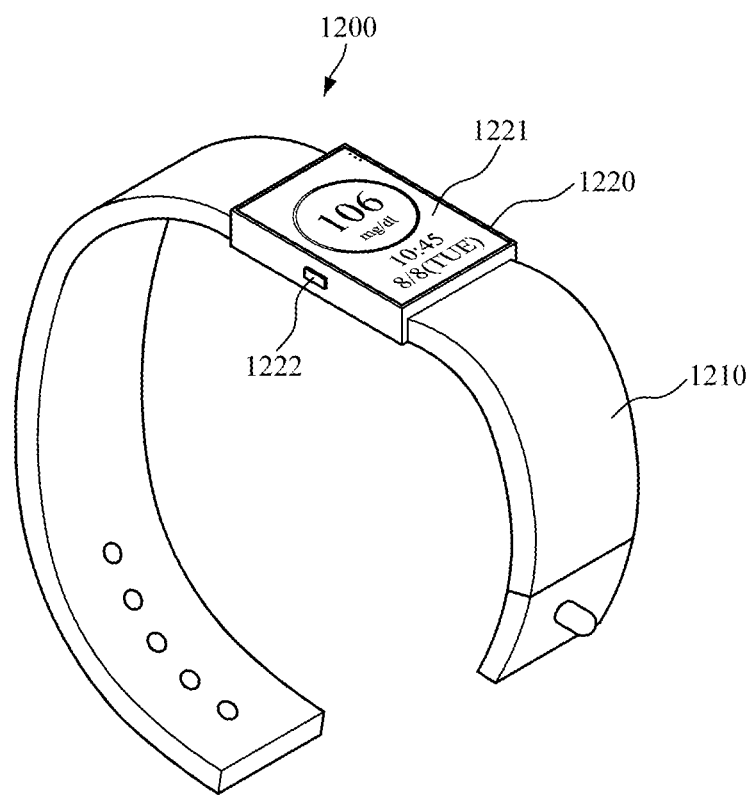
FIG. 12 is a diagram illustrating a wrist type wearable device according to an embodiment.

FIG. 12 is a diagram illustrating a wrist type wearable device.

Referring to FIG. 12, the wrist type wearable device 1200 may include a strap 1210 and a main body 1220.

The strap 1210 be may be separated into two members that are connected to each end of the main body 1220 and that are configured to be coupled to each other, or may be integrally formed in the form of a smart band. The strap 1210 may be formed of a flexible material to wrap around the wrist such that the main body 1220 can be placed on the user's wrist.

The above-described apparatuses 300, 700, or 1110 for estimating a concentration may be mounted in the main body 1220. In addition, a battery may be embedded in the main body 1220 to supply power to the wrist type wearable device 1200, and the apparatuses 300, 700, or 1110 for estimating concentration.

An optical sensor may be mounted in a lower part of the main body 1220 such that the optical sensor is exposed to the user's wrist. Accordingly, when the user wears the wrist type wearable device 1200, the optical sensor is brought into contact with the skin of the user. In this case, the optical sensor may acquire an in vivo spectrum by emitting emit light towards an object and receiving light reflected by or scattered from the object.

The wrist type wearable device 1200 may further include a display 1221 and an input interface 1222 that are mounted in the main body 1220. The display 1221 may display data processed by the wrist type wearable device 1200 and the apparatuses 300, 700, or 1110 for estimating a concentration, processing result data, and the like. The input interface 1222 may receive various operation signals based on user input.

The current embodiments can be implemented as computer readable code stored in a non-transitory computer-readable medium. Code and code segments constituting the computer program can be inferred by a person skilled in the art. The computer-readable medium includes all types of recording media in which computer readable data are stored. Examples of the computer-readable medium include a ROM, a RAM, a CD-ROM, a magnetic tape, a floppy disk, and an optical data storage. Further, the computer-readable medium may be implemented in the form of a carrier wave such as Internet transmission. In addition, the computer-readable medium may be distributed to computer systems via a network, in which computer readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating a concentration of an analyte, comprising:
   a spectrum acquisition device configured to acquire a first in vivo spectrum of an object during an estimation timeframe; and
   a processor configured to:
   estimate the concentration of the analyte by inputting the first in vivo spectrum into a concentration estimation model that is generated based on a second in vivo spectrum measured during a training timeframe in which the concentration of the analyte in the object is substantially constant; and
   at each time when a new first in vivo spectrum is acquired after the concentration of the analyte is estimated using the previous first in vivo spectrum, update the concentration estimation model based on the new first in vivo spectrum and the previously estimated concentration of the analyte.

2. The apparatus of claim 1, wherein the spectrum acquisition device is configured to acquire at least one of the previous first in vivo spectrum and the new first in vivo spectrum from an external device.

3. The apparatus of claim 1, wherein the spectrum acquisition device is configured to measure at least one of the previous first in vivo spectrum and the new first in vivo spectrum by emitting light towards the object and receiving light reflected by or scattered from the object.

4. The apparatus of claim 3, wherein the spectrum acquisition device is configured to measure at least one of the previous first in vivo spectrum and the new first in vivo spectrum using at least one of infrared spectroscopy and Raman spectroscopy.

5. The apparatus of claim 1, wherein the processor is configured to:
   generate a spectrum for updating the concentration estimation model by correcting the previous first in vivo spectrum based on the estimated concentration of the analyte;
   extract a principal component spectrum from the generated spectrum for updating the concentration estimation model [and the second in vivo spectrum used in generating the concentration estimation model]; and update the concentration estimation model using the extracted principal component spectrum.

6. The apparatus of claim 5, wherein the processor is configured to generate the spectrum for updating the concentration estimation model by removing a spectrum corresponding to a concentration change amount relative to a reference concentration of the analyte from the new first in vivo spectrum.

7. The apparatus of claim 5, wherein the processor is configured to extract the principal component spectrum from the spectrum for updating the concentration estimation model [and the second in vivo spectrum used in generating the concentration estimation model] by using at least one of principal component analysis (PCA), independent component analysis (ICA), non-negative matrix factorization (NMF), and singular value decomposition (SVD).

8. The apparatus of claim 1, wherein the analyte is at least one of glucose, triglyceride, urea, uric acid, lactate, protein, cholesterol, and ethanol.

9. The apparatus of claim 1, wherein the analyte is at lease one of glucose, triglyceride, urea, uric acid, lactate, protein, cholesterol, and ethanol.

10. The apparatus of claim 1, wherein the analyte is glucose and the timeframe in which the concentration of the analyte is substantially conssstat is a fasting timeframe.

11. A method of estimating a concentration of an analyte, the method comprising:

acquiring a first in vivo spectrum of an object during an estimation timeframe;

estimating the concentration of the analyte by inputting the first in vivo spectrum into a concentration estimation model that is generated based on a second in vivo spectrum measured during a timeframe in which the concentration of the analyte in the object is substantially constant; and at each time when a new first in vivo spectrum is acquired after the concentration of the analyte is estimated using the previous first in vivo spectrum, updating the concentration estimation model based on the new first in vivo spectrum and the previously estimated concentration of the analyte.

12. The method of claim 11, wherein the acquiring of the first in vivo spectrum comprises receiving at least one of the previous first in vivo spectrum and the new first in vivo spectrum from an external device.

13. The method of claim 11, wherein the acquiring of the first in vivo spectrum comprises emitting light towards the object and measuring at least one of the previous first in vivo spectrum and the new first in vivo spectrum by receiving light reflected by or scattered from the object.

14. The method of claim 13, wherein the measuring of the first in vivo spectrum comprises measuring at least one of the previous first in vivo spectrum and the new first in vivo spectrum using at least one of infrared spectroscopy and Raman spectroscopy.

15. The method of claim 11, wherein the updating of the concentration estimation model comprises:

generating a spectrum for updating the concentration estimation model by correcting the previous first in vivo spectrum based on the estimated concentration of the analyte;

extracting a principal component spectrum from the generated spectrum for updating the concentration estimation model [and the second in vivo spectrum used in generating the concentration estimation model]; and updating the concentration estimation model using the extracted principal component spectrum.

16. The method of claim 15, wherein the generating of the spectrum for updating the concentration estimation model comprises generating the spectrum for updating the concentration estimation model by removing a spectrum corresponding to a concentration change amount relative to a reference concentration of the analyte from the new first in vivo spectrum.

17. The method of claim 15, wherein the extracting of the principal component spectrum comprises extracting the principal component spectrum from the spectrum for updating the concentration estimation model [and the second in vivo spectrum used in generating the concentration estimation model] by using at least one of principal component analysis (PCA), independent component analysis (ICA), non-negative matrix factorization (NMF), and singular value decomposition (SVD).

18. The method of claim 11, further comprising:

acquiring the second in vivo spectrum in the timeframe in which the concentration of the analyte in the object is substantially constant;

extracting a principal component spectrum from the second in vivo spectrum in the timeframe in which the concentration of the analyte in the object is substantially constant; and generating the concentration estimation model based on the extracted principal component spectrum and a pure component spectrum of the analyte.

19. The method of claim 11, wherein the analyte is at least one of glucose, triglyceride, urea, uric acid, lactate, protein, cholesterol, and ethanol.

20. The method of claim 11, wherein the analyte is glucose, and the timeframe in which the concentration of the analyte is substantially constant is a fasting section.

* * * * *